US008372136B2

(12) United States Patent
Rangwala et al.

(10) Patent No.: US 8,372,136 B2
(45) Date of Patent: Feb. 12, 2013

(54) IMPLANTS HAVING HIGH FATIGUE RESISTANCE, IMPLANT DELIVERY SYSTEMS, AND METHODS OF USE

(75) Inventors: Hussain S. Rangwala, Edina, MN (US); Zhiyong Zhang, Edina, MN (US); Robert Wayne VanPelt, Jr., Saint Paul, MN (US); William Joseph Whealon, Chaska, MN (US)

(73) Assignee: Covidien LP, Mansfield, MA (US)

( * ) Notice: Subject to any disclaimer, the term of this patent is extended or adjusted under 35 U.S.C. 154(b) by 241 days.

(21) Appl. No.: 12/758,687

(22) Filed: Apr. 12, 2010

(65) Prior Publication Data

US 2010/0262227 A1    Oct. 14, 2010

Related U.S. Application Data

(60) Provisional application No. 61/168,215, filed on Apr. 10, 2009.

(51) Int. Cl.
*A61F 2/06* (2006.01)
(52) U.S. Cl. ........................................ 623/1.15; 606/108
(58) Field of Classification Search .................. 606/108, 606/198; 623/1.15, 1.16, 1.17
See application file for complete search history.

(56) References Cited

U.S. PATENT DOCUMENTS

| 6,743,252 | B1 | 6/2004 | Bates et al. | |
|---|---|---|---|---|
| 6,955,686 | B2 * | 10/2005 | Majercak et al. | 623/1.15 |
| 2004/0204751 | A1 | 10/2004 | Fischell et al. | |
| 2008/0215133 | A1 | 9/2008 | Richter | |
| 2009/0082848 | A1 | 3/2009 | Mori et al. | |

FOREIGN PATENT DOCUMENTS

DE    10 2005 037 863 A1    2/2007

OTHER PUBLICATIONS

Dierk Scheinert et al., "Prevalence and Clinical Impact of Stent Fractures After Femoropopliteal Stenting", Journal of the American College of Cardiology, 45(2):312-315 (2005).
Oliver Schlager et al., "Long-Segment SFA Stenting—The Dark Sides: In-Stent Restenosis, Clinical Deterioration, and Stent Fractures", J. Endovasc. Ther., 12:676-684 (2005).
International Search Report for PCT/US2010/030769, mailed Jul. 27, 2010.

* cited by examiner

*Primary Examiner* — Victor Nguyen
(74) *Attorney, Agent, or Firm* — Alana T. Bergman, Esq.

(57) ABSTRACT

According to one aspect of the present invention, a fatigue resistant stent includes a flexible tubular structure having an inside diameter, an outside diameter, and a sidewall therebetween and having apertures extending through the sidewall. According to other aspects of the invention, processes for making a fatigue resistant stent are disclosed. According to further aspects of the invention, delivery systems for a fatigue resistant stent and methods of use are provided.

19 Claims, 11 Drawing Sheets

IMPLANTS HAVING HIGH FATIGUE RESISTANCE, IMPLANT DELIVERY SYSTEMS, AND METHODS OF USE

FIELD OF THE INVENTION

The present invention relates to an implant having high resistance to fracture when mechanically cycled at a site in a body lumen. More particularly, this invention pertains to a fatigue fracture resistant vascular implant such as a self-expanding stent.

BACKGROUND OF THE INVENTION

Stents are widely used for maintaining an open lumen in a patient's body. For example, stents may be used to maintain patency of a coronary artery, carotid artery, cerebral artery, popliteal artery, iliac artery, femoral artery, tibial artery, renal artery, other blood vessels including veins, or other body lumens such as the ureter, urethra, bronchus, esophagus, tear duct, fallopian tube, nasal cavity, or other passage.

Stents are commonly metallic tubular structures made from stainless steel, Nitinol, Elgiloy, cobalt chrome alloys, tantalum, and other metals, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs. Non-bioabsorbable stents may also release drugs over time. In certain designs, stents are open-celled or closed-celled cylindrical structures. Stents are passed through a body lumen in a collapsed state. At the point of an obstruction or other deployment site in the body lumen, the stent is expanded to an expanded diameter to support the luminal wall and maintain an open lumen at the deployment site.

One type of stent is often referred to as a "balloon expandable" stent. Stent delivery systems for balloon expandable stents are typically comprised of an inflatable balloon mounted on a multi lumen tube. The stent delivery system with stent crimped thereon can be advanced to a treatment site, often over a guidewire, and the balloon inflated to expand and deploy the stent.

In the case of a shape memory stent, the stent is pre-programmed to remember a reduced diameter or shape at one temperature and an expanded diameter or shape at a higher temperature. The stent is compressed onto the distal end of a stent delivery system at a cold temperature and the stent delivery system with stent crimped thereon can be advanced to a treatment site, often over a guidewire, while being maintained below a phase change temperature of the stent. At the deployment site, the stent is warmed or allowed to warm to a higher temperature at which a phase change of the shape memory material results in expansion of the stent from a collapsed state to an expanded state.

Other stents are so-called "self expanding" stents and do not use balloons to cause the expansion of the stent. An example of a self-expanding stent is a tube (e.g., a coil tube, a mesh tube, or a tube comprised of formed wire with or without welded wire junctions) made of an elastically deformable material (e.g., a superelastic material such a nitinol). Open or closed cell stents are commonly made by laser cutting of tubes, or cutting patterns into sheets followed by or preceded by welding the sheet into a tube shape, and other methods. A very popular type of self expanding stent is made from super-elastic nitinol, for example, the EverFlex stent made by ev3, Inc. of Plymouth, Minn.

Self expanding stents are commonly secured to a stent delivery system under radial compression or under axial tension in a collapsed state. Such a system can be comprised of an outer tubular member and an inner tubular member. The inner and outer tubular members are axially slideable relative to one another. The stent (in the collapsed state) is mounted on the stent delivery system surrounding the distal end of the inner tubular member. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout at least a portion of its length such that it can be advanced over the guide wire to the deployment site. The combined structure (i.e., stent mounted on stent delivery system) is passed through the patient's lumen until the distal end of the delivery system arrives at the deployment site within the body lumen. The deployment system and/or the stent may include radiopaque markers to permit a physician to visualize positioning of the stent under fluoroscopy prior to deployment. At the deployment site, the outer sheath is retracted to expose the stent. The exposed stent is free to self-expand within the body lumen. Following expansion of the stent, the inner tube is free to pass through the stent such that the delivery system can be removed through the body lumen leaving the stent in place at the deployment site.

Stent delivery systems may be comprised of an over the wire (OTW), rapid exchange (RX), or fixed wire (FW) delivery catheter. OTW delivery catheters allow a guidewire to pass through a lumen that extends over the entire length of the delivery catheter. RX delivery catheters allow a guidewire to pass through a lumen that extends over a partial length (usually 10-30 cm) of the delivery catheter. OTW delivery catheters provide better support than RX delivery systems yet they require the use of longer guidewires which can be cumbersome to handle. FW delivery systems are very simple in that they do not have a guidewire lumen. The FW system is advanced to a treatment site without the benefit of tracking over a pre-placed guidewire. To assure that a stent can be delivered to the intended treatment site stent delivery catheters with stents mounted thereon must have at least adequate trackability, flexibility, and kink resistance and stents, once implanted, must have at least adequate radial force, kink resistance, and fatigue life.

Stents implanted in some locations can require different physical attributes than stents implanted in other locations. Stents used in coronary or renal arteries can be fairly short because the stenosed region of the vessel is generally fairly short whereas stents used in the legs often must be very long so that disease typical of leg vessels can be treated without overlapping short stents.

In other examples, stents implanted in arteries must have high pulsatile fatigue life to withstand the small diameter changes caused by the artery diameter changes that occur with every heart beat whereas stents implanted in non-vascular conduits do not require this attribute. In a further example, stents implanted in limb vessels such as the superficial femoral artery (SFA) must have high fatigue life to withstand vessel length and orientation changes that occur when the leg is bent or straightened whereas stents implanted in coronary vessels need not meet this requirement. Long stents also must be forgiving of having an implanted length quite different (usually longer) from the design length as a result of physician technique during stent implantation and the practical limitations of stent delivery systems.

Unfortunately, a common problem with stents deployed in some vessels such as the SFA is that the stents fracture over time due to the dynamic loading environment of the vessel. Problems secondary to stent fracture can include intimal hyperplasia, pain, bleeding, vessel occlusion, vessel perforation, high in-stent restenosis rate, non-uniform drug delivery profile, non-uniform vessel coverage and other problems, and re-intervention may be required to resolve the problems. Stent fracture rates in the SFA range from 2% to 28% at 1-3 years after implantation, as reported in various clinical trials (Durability I, Resilient, Scirocco and Absolute) and research papers (for example *Prevalence* and clinical impact of stent fractures after femoropoliteal stenting; J. Am. Coll. Cardiol. 2005 Jan. 18; 45(2): 312) and *Long-Segment SFA stenting—The Dark Sides: In-Stent Restenosis, Clinical Deterioration, and Stent Fractures; J Endovasc Ther* 2005; 12:676-684.

While stents commonly achieve high pulsatile fatigue life, they often have insufficient resistance to fracture under in-patient loading conditions other than pulsatile, such as longitudinal extension, torsion, and flexion, as is appropriate for some implantation sites. Stents implanted in the popliteal artery, iliac artery, femoral artery, tibial artery, carotid, femoral-popliteal and other sites can suffer from large amounts of axial, flexural, or torsional cyclic loading. Recent data has indicated that some stents, such as those implanted in the SFA, must withstand axial elongation/compression of up to 35% as implanted. While attempts have been made to improve the fatigue resistance of implantable stents, an implant having suitable attributes (especially high fatigue life) for these demanding anatomical locations has yet to be developed.

What is needed is a stent that can be easily manufactured and that will survive without fracture when implanted in locations that experience high mechanical forces produced by patient activity in addition to those forces produced by the beating heart. Also needed is a stent which will have high fatigue life after implantation and a stent that will survive without fracture despite elongation during implantation.

SUMMARY OF THE INVENTION

According to one aspect of the present invention, a fatigue resistant stent comprises a flexible tubular structure having an inside diameter, an outside diameter, and a sidewall therebetween and having apertures extending through the sidewall. According to other aspects of the invention, processes for making a fatigue resistant stent are disclosed. According to further aspects of the invention, delivery systems for a fatigue resistant stent and methods of use are provided.

BRIEF DESCRIPTION OF THE DRAWINGS

The above and further advantages of the invention may be better understood by referring to the following description in conjunction with the accompanying drawings in which.

DETAILED DESCRIPTION

With reference now to the various drawing figures a description is provided of embodiments that are examples of how inventive aspects in accordance with the principles of the present invention may be practiced. It is to be understood that both the foregoing general description and the following detailed description are exemplary and explanatory only and are not restrictive of the broad inventive aspects disclosed herein. It will also be appreciated that the inventive concepts disclosed herein are not limited to the particular stent configurations disclosed herein, but are instead applicable to any number of different stent configurations.

Figure 1:
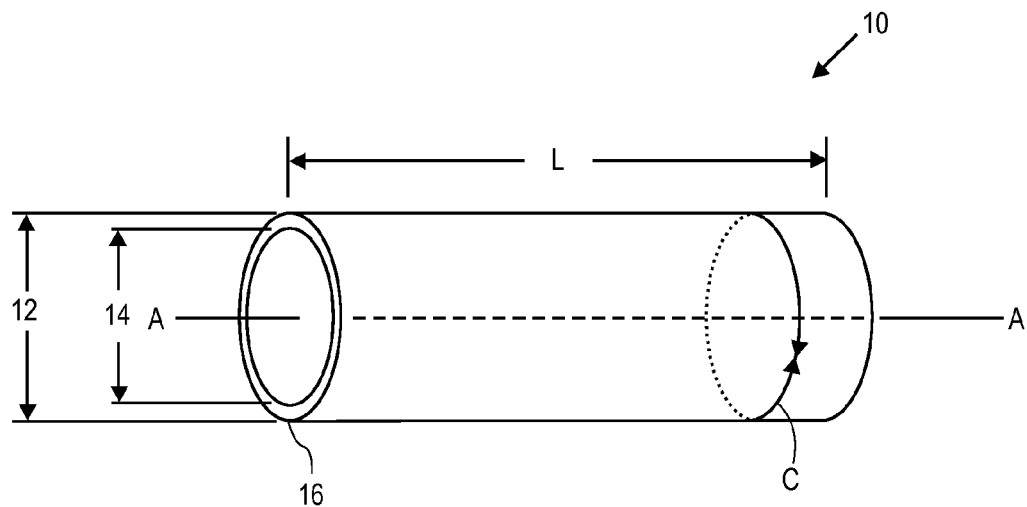
FIG. 1 illustrates a schematic isometric view of one embodiment of a prior art stent.
Figure 2:
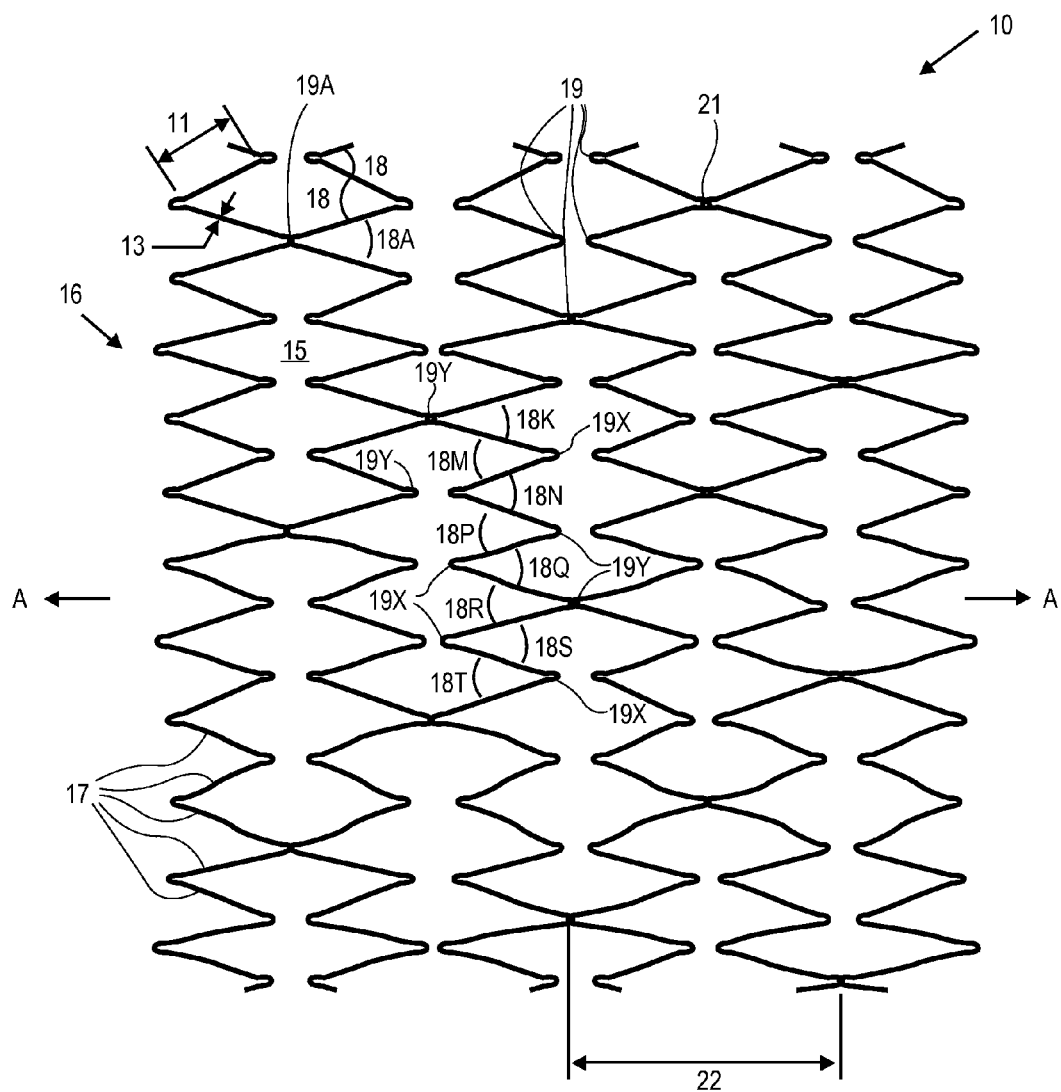
FIGS. 2 and 2A illustrate an enlarged view of a portion of the stent of FIG. 1. The stent is shown diametrically expanded and the stent structure is shown cut longitudinally and laid flat.

FIGS. 1 and 2 illustrate prior art stent 10 having a length L, an outer circumference C, and a longitudinal axis A-A. FIG. 2 shows a portion of prior art stent 10 fully diametrically expanded, cut longitudinally parallel to axis A-A, and laid flat. Stent 10 is comprised of a tube having outer diameter 12, inner diameter 14 and wall 16 having a thickness. Openings are cut into wall 16 to form cells 15 (shaded in FIG. 2) and struts 17. Each individual strut has a length 11 between apices 19 and a thickness 13. Adjacent struts are joined at apices 19, 19A and have an intersection angle 18, 18A. Adjacent cells are joined by connectors 21. Connectors 21 on opposite sides of cell 15 are circumferentially offset from one another. Circumferentially offset connectors provide stent 10 with increased axial, bending and torsional flexibility and improved kink resistance when compared to other stent designs having connectors 21 directly opposed along axis A-A. Cell length 22 can be defined as the length in the direction of axis A-A between connectors 21 at either end of a cell.

Stent 10 can be made from stainless steel, Nitinol, Elgiloy, cobalt chrome alloys, tantalum, and other metals, or polymers, can be a permanent enduring implant, can be bioabsorbable at least in part, and may elute over time substances such as drugs. Cells 15 of stent 10 may be formed by means such as laser cutting followed by processes such as microgrit blasting to remove slag, electropolishing to remove stent material having heat affected zone and other imperfections, and surface passivation to render surface of the stent more resistant to corrosion.

When diameter 12 of stent 10 is reduced the associated reduction in stent circumference C is accommodated by reduction in angle 18 between struts with associated increase in bending strain in struts 17 and especially in the vicinity of apices 19. The amount of strain concentrated near the apices can be calculated using finite element analysis (FEA, discussed below) or by other methods.

Figure 2A:
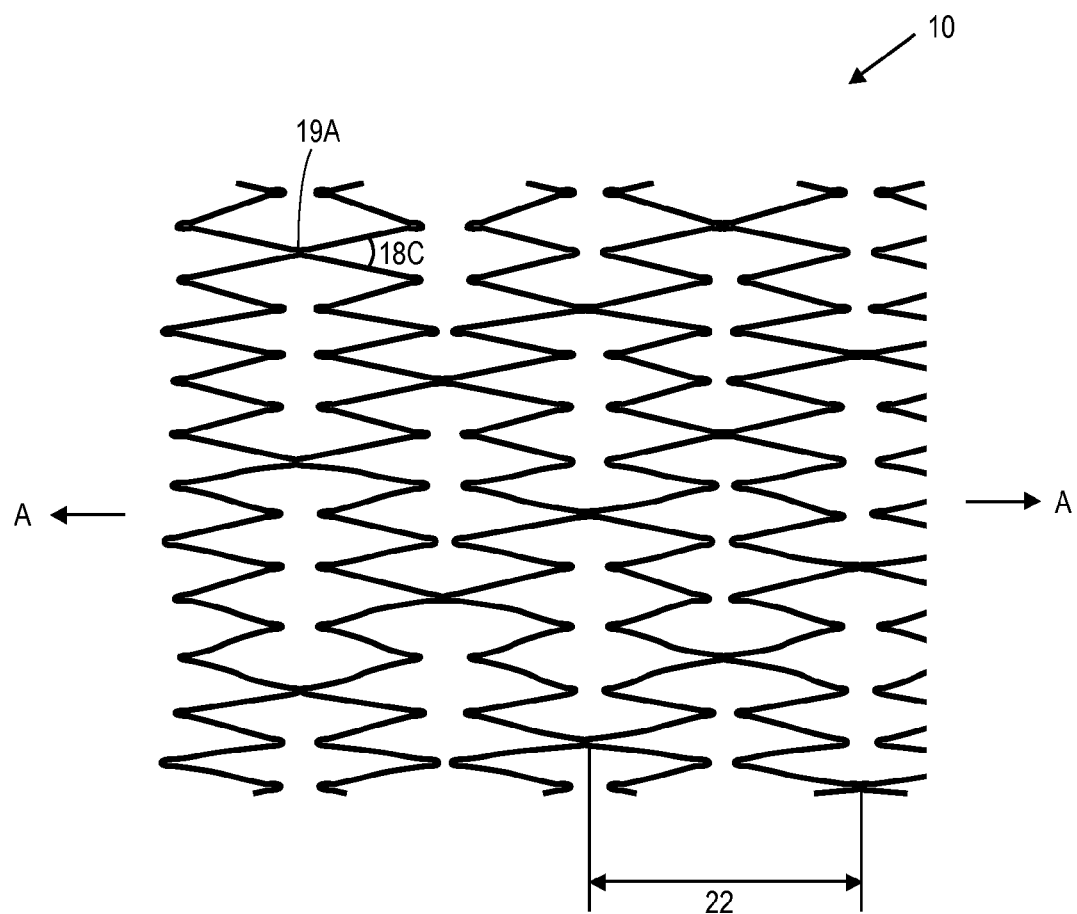

The strain in a single strut in the vicinity of an apex can also be approximated with the help of the following formula (with reference to FIGS. 2 and 2A). In FIG. 2A stent 10 has been reduced in circumference with no change in length 22 as compared to stent 10 in FIG. 2. The strain induced in the strut near apex 19A by this change is calculated as follows:

$$\text{Change in Strain in strut} = \frac{SW[\sin(\theta 2) - \sin(\theta 1)]}{[LS - SW\sin(\theta 2)]}$$

where:
LS=Length of Strut 11
SW=Strut Width 13
θ2=Final Angle 18c
θ1=Initial Angle 18A In the case of a stent having no strain in the strut near an apex when the stent is fully expanded (as is usually the case for a self-expanding stent), the initial strain in the strut near the apex is zero, so the strain in the strut near the apex of the stent when deformed equals that calculated using the above formula. Importantly, from the formula we learn that the calculated change in strut strain is lower when the change in angle 18 is lower, lower when the strut width SW is less, and lower when the strut length LS increases.

The maximum strain in a deformed stent is called the peak strain. The peak strain typically occurs in a single strut in the vicinity of an apex although it may occur elsewhere in the stent depending on the details of stent design. Predominant strains in stents may be tensile (usually defined as positive) or compressive (usually defined as negative). Stents in some implant locations, for example the SFA or popliteal artery, can suffer bending strains and torsional strains in addition to the tensile and compressive strains mentioned above. In some stent embodiments such torsional and bending strains on the stent will resolve primarily into tensile or compressive strains in the vicinity of stent apices. High tensile strains can cause cracks to initiate and propagate through the stent, leading to reduced fatigue life and stent fracture. Compressive strains do not tend to open cracks so generally do not cause reduced stent life unless the magnitude of the strain is extraordinary. Some portions of a deformed stent may be highly strained during use while other portions may not be strained at all, said latter portions having zero strain. A deformed stent can be thought of as a collection of tiny volumetric regions, each region having a strain level; collectively the strain levels of the regions range from a maximum negative value to a maximum positive value. For a stent in service in the body, if stent strains are maintained below the endurance limit of the stent material then high fatigue life may be expected provided the stent material has undergone proper materials processing, surface finishing and has suitable biocompatibility characteristics. However, if a stent in service in the body suffers stent strains above the endurance limit of the stent material then high fatigue life cannot be expected regardless of stent material processing, surface finishing and biocompatibility characteristics.

Commonly prior art stents such as stent 10 are designed such that the strain in the stent remains at a low level under pulsatile loading conditions, i.e. under oscillating circumferential compressive strains. Stent 10 is also known to accommodate a limited amount of axial elongation (at most about 10-15%) without compromising pulsatile fatigue life. This limited amount of axial elongation is suitable for some stent implant locations. However, it has been determined that stents implanted in other locations, for example the SFA or popliteal arteries, can subject a stent to very large elongations. For example the leg can impart ±5% elongation due to normal leg motion and the doctor may impart as much as 30% elongation and possibly more to the stent during stent implantation. In addition the stent may be loaded in torsion, and in bending as well due to normal leg motion.

Figure 1A:
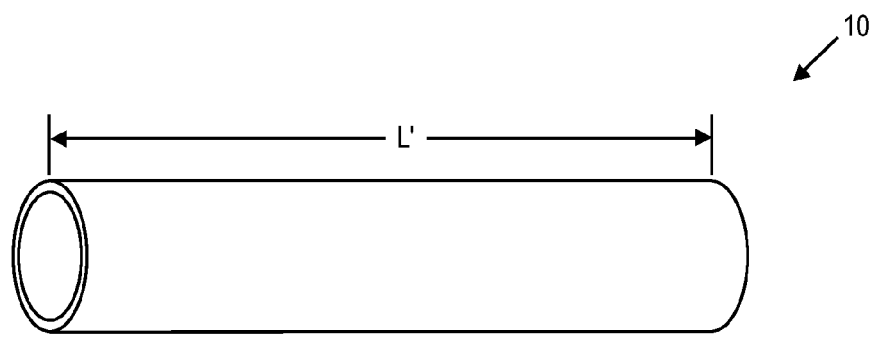
FIG. 1A schematically illustrates the stent of FIG. 1 with the stent elongated axially.
Figure 3:
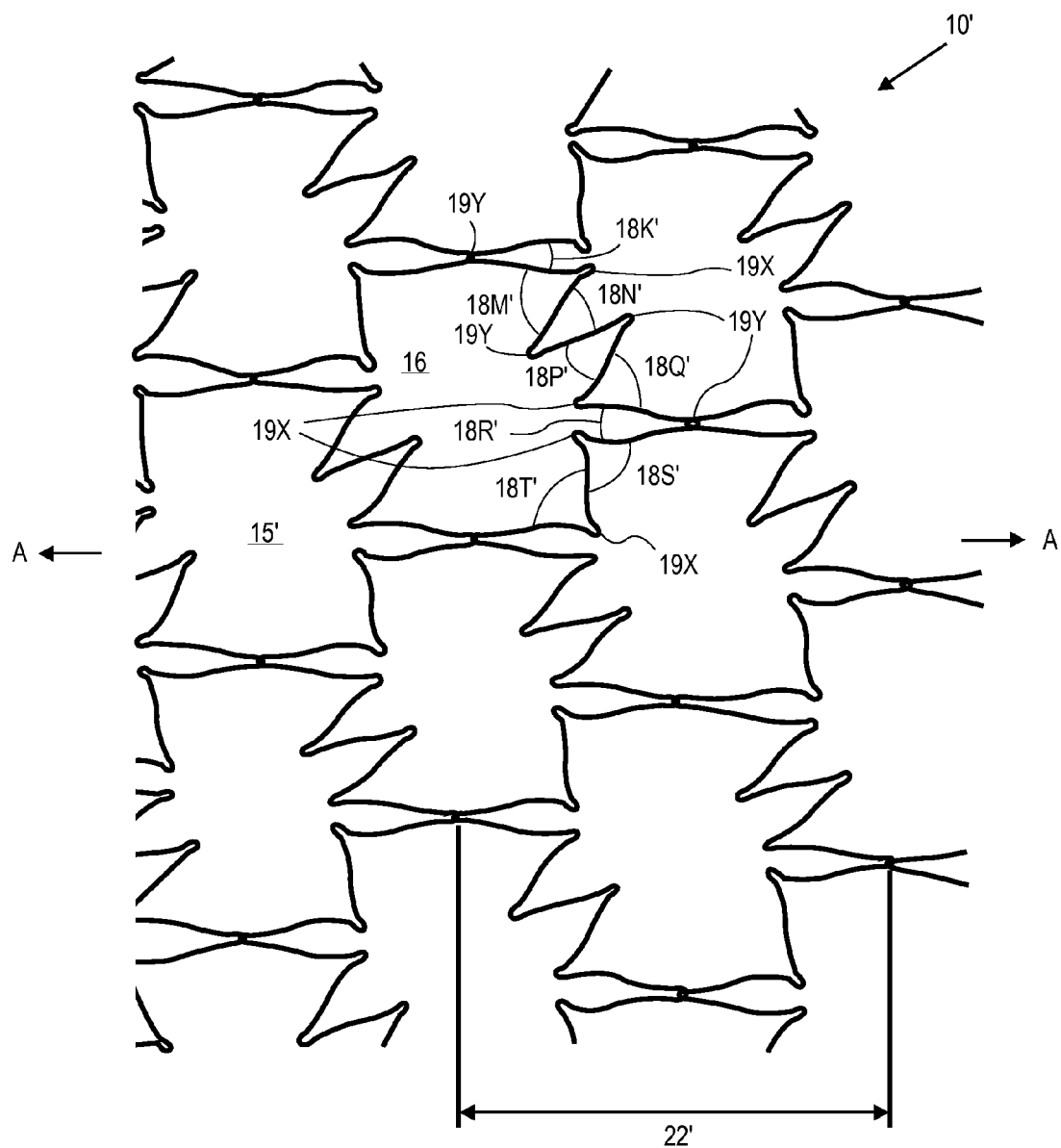
FIG. 3 illustrates the stent of FIG. 2 with the stent elongated axially. The stent is shown diametrically expanded and the stent structure is shown cut longitudinally and laid flat.

Stent percent elongation can be defined as a change in length of a stent cell along axis A-A. FIG. 1 shows stent 10 at rest and having a length L as previously defined. FIG. 1A shows stent 10 elongated by 50% and having a length L'. Stent elongation is defined as the increase in length (stretched length L' minus unstretched length L) divided by the unstretched length L. If the stent has been uniformly elongated over its entire length then each stent cell will be elongated by the same amount as that of the stent overall. FIG. 2 shows un-elongated stent 10 having a cell length 22 as previously defined. FIG. 3 shows stent 10 elongated by 50% and having a cell length 22'. Cell elongation is defined as the increase in cell length (cell length 22' minus cell length 22) divided by the unstretched cell length 22. In practice it is found that stent elongation is generally not uniform over the length of the stent, with some cells elongated more than others. It is also sometimes seen that some cells are shortened, i.e., some cells have a negative calculated elongation. It is also possible for stent overall lengths to be shortened. Stent elongation is a useful surrogate model for the prediction of stent fatigue life under more complex loading conditions. Stent elongation can cause high tensile strains in the vicinity of stent apices that can be representative of the strains imparted by more complex loading conditions such as when a stent is subjected to a combination of elongation, torsion, and bending.

FIG. 3 illustrates stent 10 elongated 50% axially, denoted as stent 10' in the elongated condition. Stent 10' is shown diametrically expanded, cut longitudinally parallel to axis A-A and laid flat. Stent 10' cell geometry is substantially distorted from the geometry of stent 10 (FIG. 2). The distortion can be visualized by comparing angles 18 in the elongated stent 10' to those in the non-elongated stent 10. It can be seen that angles 18K, 18N, 18P and 18r have reduced to angles 18K', 18N', 18P' and 18r' respectively while angles 18M, 18Q, 18S and 18T have increased to angles 18M', 18Q', 18S' and 18T' respectively. The distorted cell geometry seen in FIG. 3 causes reduced fatigue life of elongated stent 10' by increasing the tensile strain in some stent struts to high levels.

Specifically, as illustrated in FIG. 3, the tensile strain in the strut near apices 19X has increased because of the increased angles 18M', 18Q', 18S' and 18T' between some struts, thereby exposing the struts near apices 19X to lower fatigue life. At other regions of the stent cell 15, struts near apices 19Y are loaded in compression due to the decreased angles 18K, 18N, 18P and 18r between struts, thereby permitting the struts near apices 19Y to sustain higher fatigue life. Stated another way, elongation of stent 10 results in concentration of tensile strains in the stent volume in the vicinity of apices 19X and concentration of compressive strains in the stent volume in the vicinity of apices 19Y.

Figure 4A:
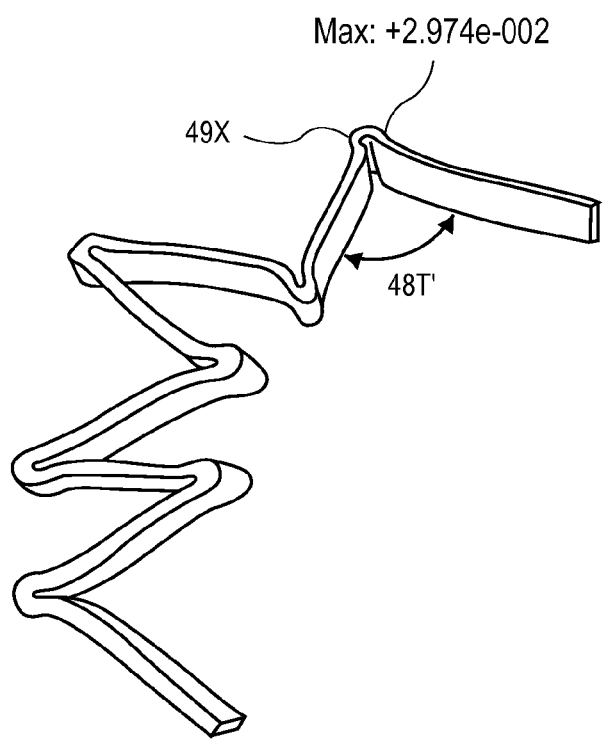
FIG. 4A illustrates an isometric view of a portion of the stent in FIG. 4 with indicia of calculated strain distributions within the stent.
Figure 4:
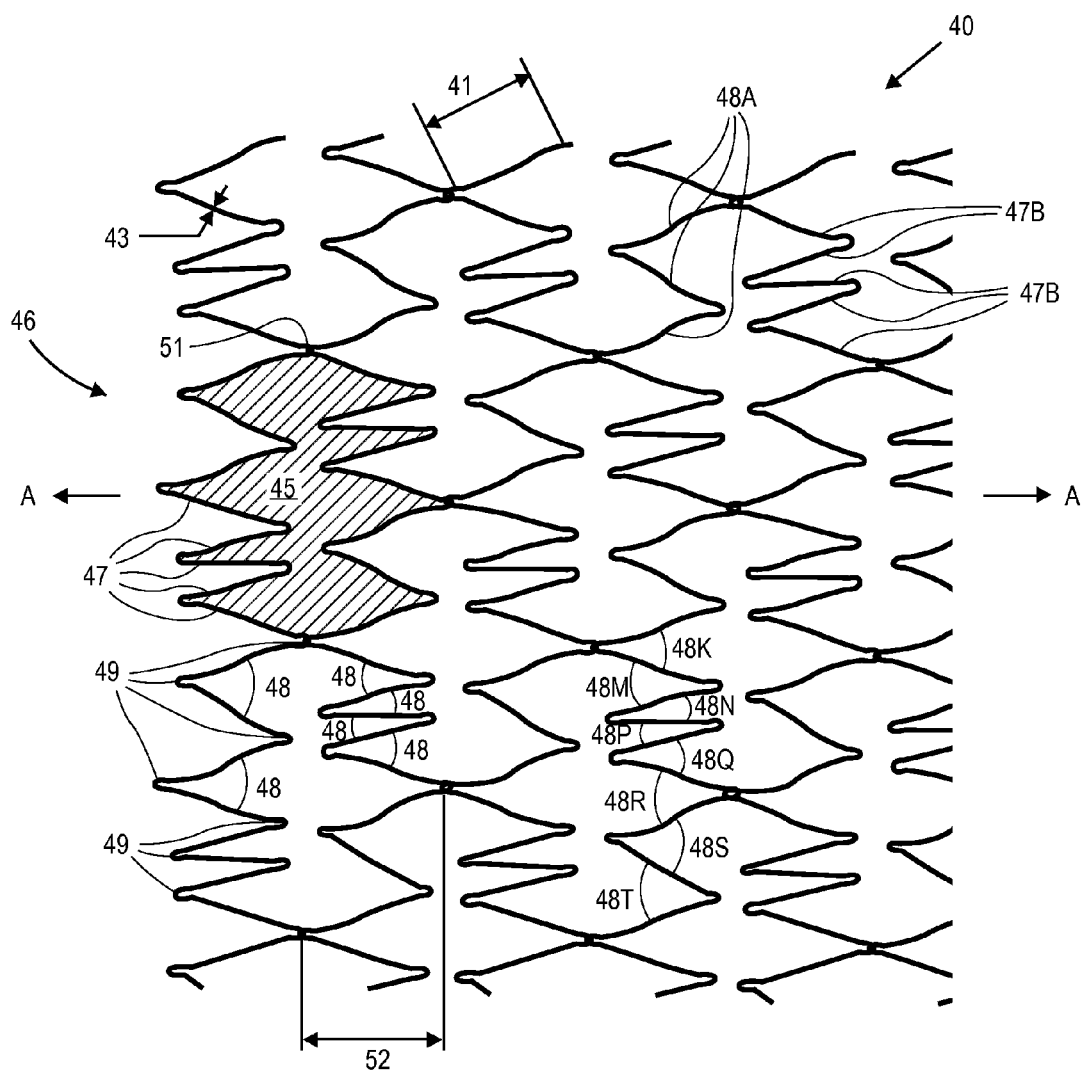
FIG. 4 illustrates a portion of a fatigue resistant stent in accordance with the principles of the present disclosure. The stent is shown diametrically expanded and the stent structure is shown cut longitudinally and laid flat.

FIG. 4 illustrates one embodiment of an inventive stent that, when elongated, has few or no highly tensioned regions. Stent 40 has a length, an outer circumference, and a longitudinal axis A-A. In FIG. 4 a portion of stent 40 is shown fully diametrically expanded, cut longitudinally parallel to axis A-A, and laid flat. Stent 40 is comprised of a tube having an outer diameter, an inner diameter and a wall 46 having a thickness. Openings are cut into wall 46 to form cells 45

(shaded in FIG. 4) and struts 47, and cells 45 have a perimeter comprised of the length of the opening bounded by struts 47. Each individual strut has a length 41 between apices 49 and a thickness 43. Adjacent struts are joined at apices 49 and have an intersection angle 48. Adjacent cells are joined by connectors 51. In some embodiments connectors 51 on opposite sides of cell 45 are aligned along axis A-A. In these embodiments the asymmetry of the cell 45 perimeter, which is comprised of relatively thinned struts (discussed below) over a portion of the cell perimeter, provide stent 40 with increased axial, bending and torsional flexibility and improved kink resistance when compared to other stent designs having connectors 51 directly opposed along axis A-A. In other embodiments connectors 51 on opposite sides of cell 45 are circumferentially offset from one another. Circumferentially offset connectors can also provide stent 40 with increased axial, bending and torsional flexibility and improved kink resistance when compared to some stent designs having connectors 51 directly opposed along axis A-A. Cell length 52 can be defined as the length in the direction of axis A-A between connectors 51 at either end of a cell.

In some embodiments, stent 40 may be comprised of stainless steel, Nitinol, Elgiloy, cobalt chrome alloys, tantalum, and other metals, or polymers, may be a permanent enduring implant, may be bioabsorbable at least in part, and may elute over time substances such as drugs. In some embodiments, stent cells 45 of stent 40 may be formed by means such as laser cutting, followed by processes such as microgrit blasting to remove slag, electropolishing to remove stent material having heat affected zone and other imperfections, and surface passivation to render surface of the stent more resistant to corrosion. Stent 40 may be comprised of self-expanding, shape memory, or balloon expandable characteristics. In various embodiments stent 40 may be prepared from a tube using processes such as laser cutting, chemical etching, punching, grinding, drilling, EDM, or other processes. In other embodiments stent 40 may be prepared by cutting patterns into sheets followed by or preceded by welding the sheet into a tube shape, by electroforming the stent onto a suitable pattern or mold or by other methods. In further embodiments stent 40 is prepared by intertwining, joining, overlaying, weaving, braiding, knitting, circular knitting, compressing, or otherwise assembling filaments or wire. Filaments or wire may be joined at one or more regions where they overlap by sintering, bonding, soldering, fusing, welding, or other means. In structures so formed struts 47 of stent 40 are comprised of the length of filament or wire between joined regions and apices 49 of stent 40 are comprised of the joined regions.

Struts 47 of stent 40 have been modified as compared to struts 17 of stent 10. Struts 47B are thickened along the circumferential direction of the stent and struts 47A are both lengthened along the axial direction of the stent and thinned along the circumferential direction of the stent. In all other dimensional and materials processing aspects stent 40 is similar to stent 10. As a result of the strut modifications described above, stent 40, when elongated, has improved fatigue life compared to that of similarly elongated stent 10 (i.e. stent 10'). The improved fatigue life is accomplished because the strut modifications described prevent development of high tensile strains in the vicinity of apices 49 when stent 40 or one or more cell 45 is elongated, bent, or twisted.

Figure 5:
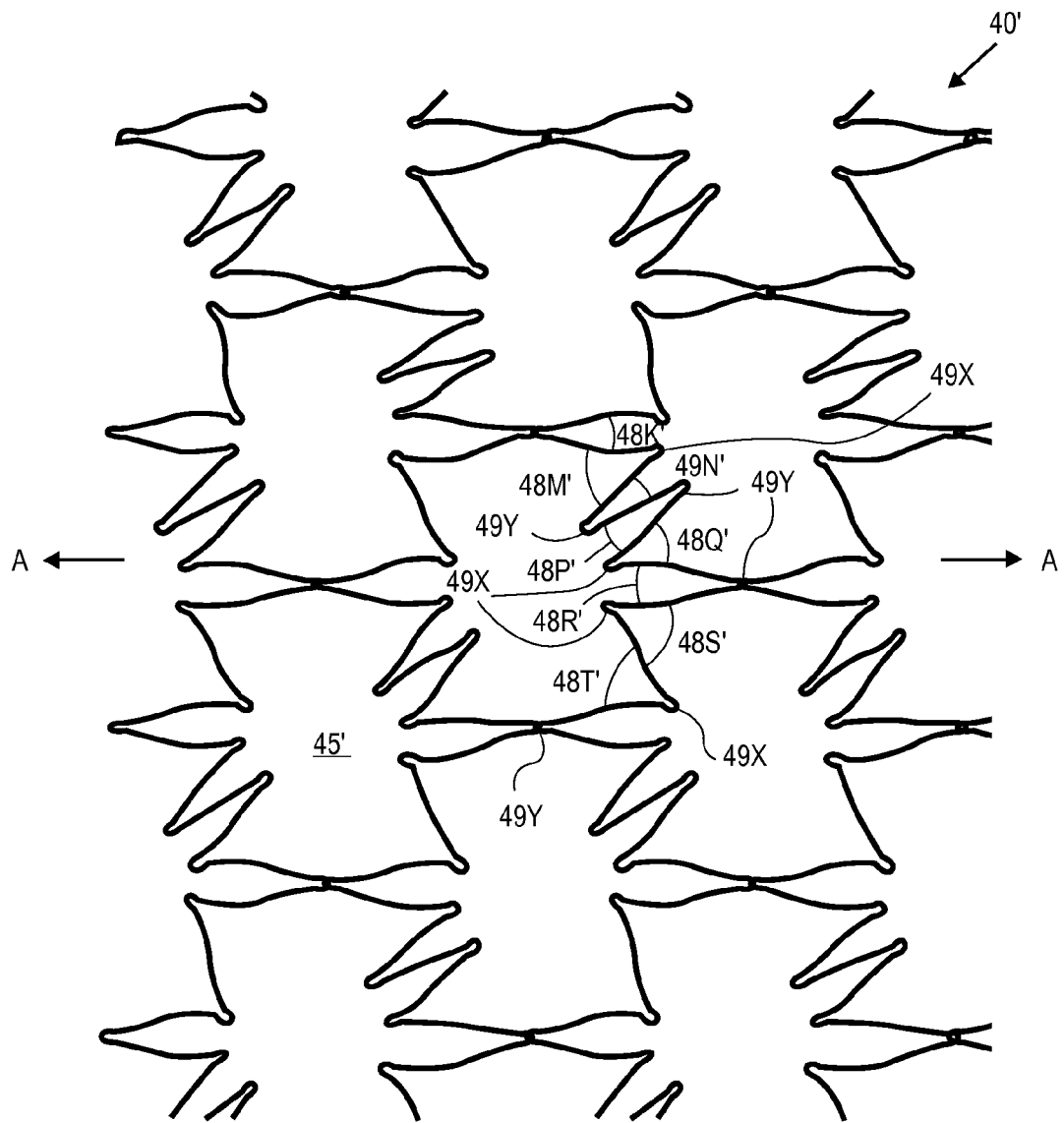
FIG. 5 illustrates the stent of FIG. 4 with the stent elongated axially. The stent is shown diametrically expanded and the stent structure is shown cut longitudinally and laid flat.

FIG. 5 illustrates stent 40 elongated 50% axially, denoted as stent 40' in the elongated condition. Stent 40' is shown fully diametrically expanded, cut longitudinally parallel to axis A-A and laid flat. Stent 40' cell geometry 45' is distorted from the geometry of stent 40. The distortion can be visualized by comparing angles 48 in the elongated stent 40' to those in the non-elongated stent 40. It can be seen that angles 48K, 48N, 48P and 48R have reduced to angles 48K', 48N', 48P' and 48R' respectively while angles 48M, 48Q, 48S and 48T have increased to angles 48M', 48Q', 48S' and 48T' respectively. Unlike stent 10', the tensile strain induced by elongation of stent 40 or of one or more cell 45 in the vicinity of apices 49X, while increased, has increased to an acceptable level because increased thickness of struts 47B limits the amount of increase to angles 48M', 48Q' and the thinner and longer struts 47A reduce the tensile strain induced in the vicinity of apices 49X when angles 48S', 48T' are increased.

Stated another way, elongation of stent 40 or of one or more cells 45 results in less concentration of tensile strains in the stent volume in the vicinity of apices 49X and more concentration of compressive strains in the volume in the vicinity of apices 49Y. The elongated cell geometry seen in FIG. 5 allows improved fatigue life of elongated stent 40' by limiting the tensile strain to acceptable levels in the vicinity of stent cell apices.

Stent 40 has another characteristic that improves its fracture resistance and fatigue life when deployed in a treatment location. Within the interior of cell 45, apices 49 are not directly opposed to one another along axis A-A, instead they are circumferentially offset from one another. Accordingly when stent 40 suffers axial compression (negative calculated elongation) non-opposed apices will not collide with or rub against each other. Such collisions or abrasion of opposed apices can cause stent surface defects to form, which can propagate with cycling over time, leading to stent fracture.

Another method of calculating material strain in the vicinity of apices involves the use of Finite Element Analysis (FEA). In one method, a commercially available FEA software package (Abaqus) was utilized to calculate the strains. Key modeling parameters were as follows: use of a 20-node three dimensional brick shape second order continuum element; use of high local mesh density in high strain regions and lower mesh densities in low strain regions; and proper mesh transitions between the higher and lower mesh density regions (i.e., brick face aspect ratio's of 10 or less and included angles of the bricks between 45 and 135 degrees). To balance simulation convergence speed and computing time with simulation accuracy, trial runs were performed for high strain regions and suitable mesh density was chosen at the density where finer mesh did not change results within tolerance.

Stent material properties were determined by tensile test on coupons having the same composition and similar thermo-mechanical history as the stent being modeled. Stent final geometry was determined by modeling precursor tubing and the effects of the stent manufacturing process (heat expansion, annealing, filing, honing, sand blasting and electrolytic polishing) on the modeled tubing, although other means of determining final stent geometry could be used. The final stent geometry determined by the above modeling was strained in an FEA simulation under tensile loading conditions and the maximum principal strains, mean strains and amplitude of the strains under static conditions were calculated. The final stent geometry determined by the above modeling was also strained in an FEA simulation under loading conditions of a superficial femoral artery implant location, including compaction, extension, uniaxial tensile repetitive load for fatigue, walking, and stair climbing loads. The maximum principal strains, mean strains and amplitude of the strains under cyclic conditions were calculated and fatigue life of the strained stent was predicted.

Figure 3A:
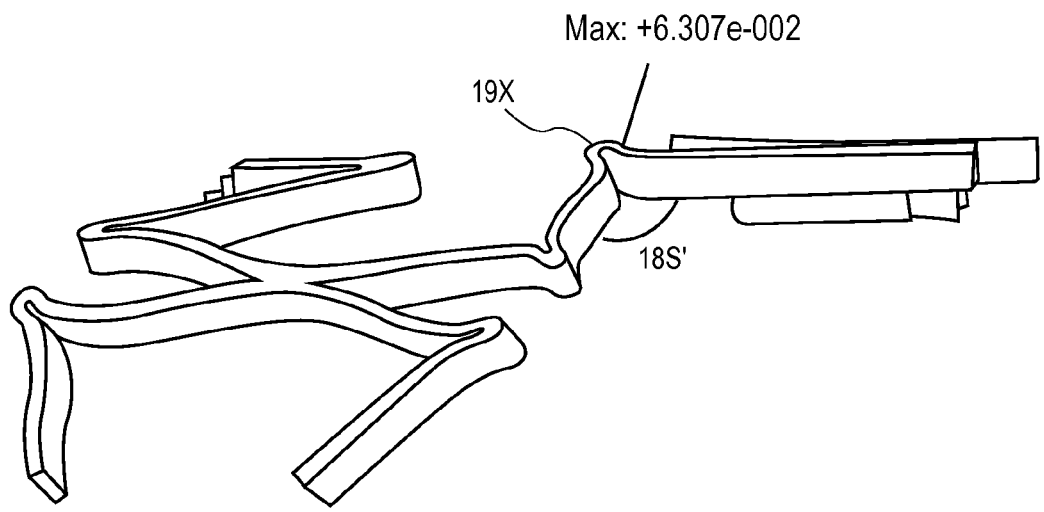
FIG. 3A illustrates an isometric view of a portion of the stent in FIG. 3 with indicia of calculated strain distributions within the stent.

FIG. 3A illustrates partial results of an FEA analysis of strains in stent 10' (stent 10, elongated by 50%). Only the portion of stent 10' having the highest strain is illustrated. It can be seen that the peak tensile strain of 6.3% is in the vicinity of apex 19X opposite angle 18S'. Due to the high tensile strain in the strut near this apex the strut is susceptible to low fatigue life. Also, averaging the highest strain in the vicinity of each of the 16 apices of cell 15 shows that the average strain in the vicinity of the apices is 3.0%±2.6%.

FIG. 4A illustrates partial results of an FEA analysis of strains in stent 40' (stent 40, elongated by 50%). Only the portion of cell 45' having the highest strain is illustrated. It can be seen that the peak tensile strain of 2.97% is in the vicinity of apex 49X opposite angle 48T'. Due to the reduced tensile strain compared to prior art the strut near this apex can sustain improved fatigue life compared to stent 10. Also, averaging the highest strain in the vicinity of each of the 16 apices of cell 45' shows that the average strain in the vicinity of the apices is 2.6%±0.6%, also an improvement over prior art stent 10 due to both the lower average strain and the reduced variation in strain. The reduced variation in strain causes the radial expansile force of the stent, as determined along the circumference of the stent, to be more uniform. Therefore a stent designed according to the teachings above will have more uniform deployment characteristics and will more uniformly resist vessel forces tending to reduce the deployed diameter of the stent.

The average strains in the vicinity of the 16 apices of cell 45, 45' in stent 40 have been further characterized at various amounts of elongation using FEA analysis. These results are shown in the table below.

| Cell Elongation (%) | Average Strain | Standard Deviation of Average Strain |
|---|---|---|
| 0 | 0.0 | 0.0 |
| 5 | 0.2 | 0.0 |
| 10 | 0.4 | 0.1 |
| 15 | 0.6 | 0.2 |
| 20 | 1.0 | 0.4 |
| 25 | 1.4 | 0.4 |
| 30 | 2.0 | 0.4 |
| 50 | 2.6 | 0.6 |

While stent 40 has the strain and elongation characteristics as described above, stents designed according to the teachings herein having other strain and elongation characteristics are contemplated. In some embodiments an inventive stent can be elongated 10%, 15%, 20%, 25%, 30%, 35%, 40%, 45% or 50% with peak strain remaining below 0.5%. In other embodiments an inventive stent can be elongated 10%, 15%, 20%, 25%, 30%, 35%, 40%, 45% or 50% with peak strain remaining below 1%, or below 2%, or below 3%, or below 4%, or below 5%. In other embodiments a stent designed according to the teachings herein can have any peak strain and elongation combination as recited in this paragraph where the standard deviation of the peak strain is one of 0.3 percent strain, 0.5 percent strain, or 1.0 percent strain.

In other embodiments stents designed according to the teachings herein having various stent cell strain and elongation characteristics are contemplated. In some embodiments an inventive stent cell can be elongated 10%, 15%, 20%, 25%, 30%, 35%, 40%, 45% or 50% with peak strain in the vicinity of the apices of the cell remaining below 0.5%. In other embodiments an inventive stent cell can be elongated 10%, 15%, 20%, 25%, 30%, 35%, 40%, 45% or 50% with peak strain in the vicinity of the apices of the cell remaining below 1%, or below 2%, or below 3%, or below 4%, or below 5%. In other embodiments a stent cell designed according to the teachings herein can have any peak strain and elongation combination as recited in this paragraph where the standard deviation of the peak strain is one of 0.3 percent strain, 0.5 percent strain, or 1.0 percent strain.

Stents have been manufactured according to the principles of the invention and have been found to have desirable strain distributions and exceptional fatigue resistance as shown in the examples below. The exemplar and competitive stents were tested for fatigue endurance according to the following methods.

Uni-axial Testing Method: Using a Bose 3300 uni-axial testing machine stent life can be determined from a step fatigue test method. According to the method, step 1 consists of elongating a stent sample to the mean strain tabulated for step 1 followed by oscillating the sample length at 40 Hz for 500,000 cycles along the direction of axis A-A to the cyclic strains tabulated for step 1. If the sample does not fracture during step 1, the sample is additionally subjected to step 2. Step 2 consists of stretching and oscillating the sample as performed in step 1 but at different pre-specified mean and cyclic strains as tabulated for step 2. If the sample does not fracture during step 2, the sample is additionally sequentially stretched and oscillated for 500,000 cycles at each subsequent step (as tabulated below) until the sample fractures. The mean strain of the step at which sample fracture occurs is recorded as the stents mean strain to failure. The fatigue tests were carried out with samples immersed in 37° C. water and specialized fixturing was used to grip the ends of individual stent samples. Strain values are calculated based on the initial length between grips of unstrained sample.

| Step | Mean Strain (%) | Cyclic Strain Amplitude (±%) |
|---|---|---|
| 1 | 11.67 | 1.30 |
| 2 | 13.89 | 1.54 |
| 3 | 16.11 | 1.79 |
| 4 | 18.33 | 2.04 |
| 5 | 20.56 | 2.28 |
| 6 | 22.78 | 2.53 |
| 7 | 25.00 | 2.78 |
| 8 | 27.22 | 3.02 |
| 9 | 29.44 | 3.27 |
| 10 | 31.67 | 3.52 |
| 11 | 33.89 | 3.77 |
| 12 | 36.11 | 4.01 |
| 13 | 38.33 | 4.26 |
| 14 | 40.56 | 4.51 |
| 15 | 42.78 | 4.75 |
| 16 | 45.00 | 5.00 |
| 17 | 47.22 | 5.25 |
| 18 | 49.44 | 5.49 |
| 19 | 51.67 | 5.74 |

This method is well suited for both quick and long-term durability studies. It allows adjusting the mean strain and cyclic strain applied on the test sample. These parameters can be finely tuned to mimic the actual mean and cyclic strain values that a particular clinical environment can impose on an implanted stent.

Multi-axial Peripheral Stent (MAPS) Fatigue Testing Method: This system was developed by Bose Corporation (model 9400 multiaxial peripheral stent test instrument) and it simulates the dynamic loading applied by peripheral arteries on a stent due to bending, twisting, extension, compression and radial distention caused for example by day-to-day activities like walking, sitting and stair climbing. Stents were deployed with 8±2% elongation in latex tubes having mechanical properties similar to those of healthy peripheral vessels, the tubes with stents therein were mounted on the tester, and phosphate buffered saline maintained at 37° C. was allowed to flow through the stents at ~64 ml/min and negligible pressure. In one cycle the deployed stents were simultaneously stretched 3.5% along stent axis A-A and twisted around axis A-A by 0.8° per mm of length; then the axes of the deployed stents were bent over a 20 mm radius curve placed at the midpoint of the stent, from 0° (no bending—stent axis A-A is straight) to 69°; then un-bent back to 0°, then simultaneously un-twisted and shortened 3.5% to the initial starting configuration. This stretching, twisting, bending, unbending, untwisting and unstretching cycle occurs at a frequency of 1.5 Hz. The number of cycles sustained by the stent before fracture occurs is recorded as the stent cycles to failure.

EXAMPLE 1

Figure 6:
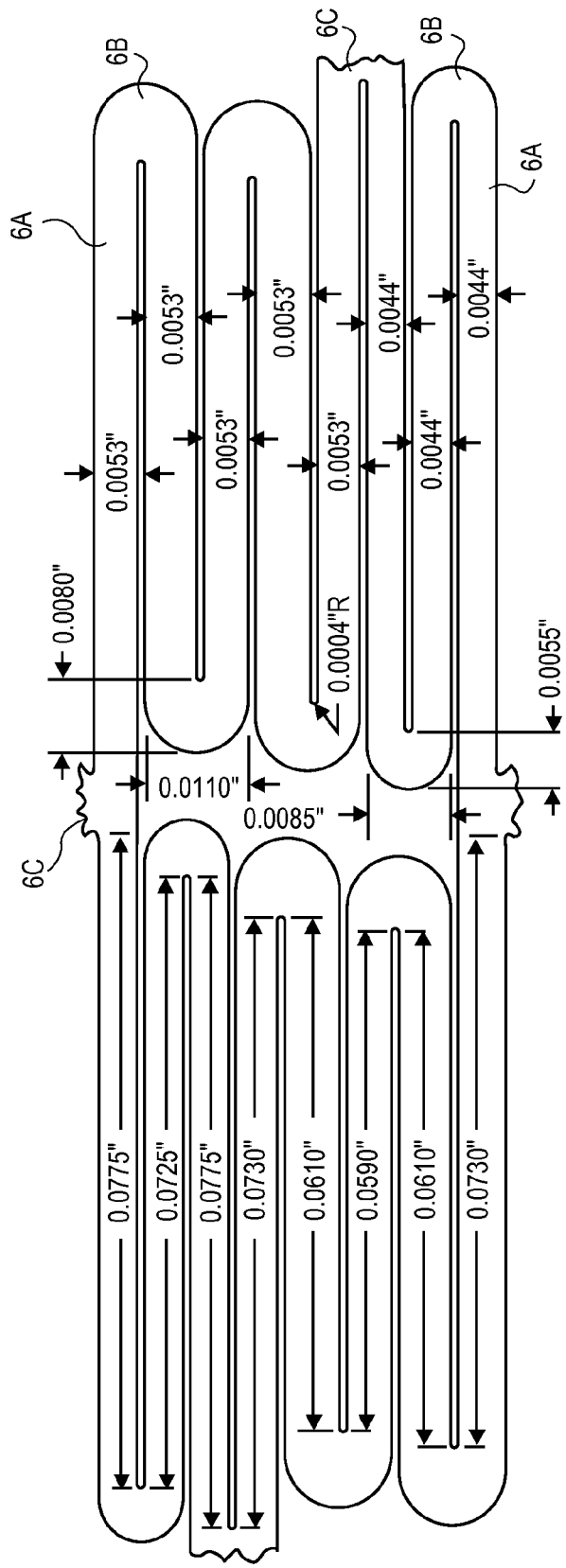
FIGS. 6 and 7 illustrate scale drawings of the geometry and dimensions of exemplar stent cells. The stent cells are shown diametrically compressed and the stent structure is shown cut longitudinally and laid flat.

A 6 mm diameter×80 mm long stent having structure as shown in FIG. 6 was laser cut from binary nitinol alloy tubing, diametrically expanded, heat treated, filed, microgrit blasted, electropolished and passivated (hereafter designated as sample 6). The final (nominal) dimensions (e.g., longitudinal dimensions and strut widths) of each cell of stent sample 6 are shown in FIG. 6; the nominal wall thickness of the stent struts 6A, apices 6B, and connectors 6C was 0.0095 inches. The sample was tested for fatigue life versus competitive stents of the same diameter using the methods described above.

EXAMPLE 2

Figure 7:
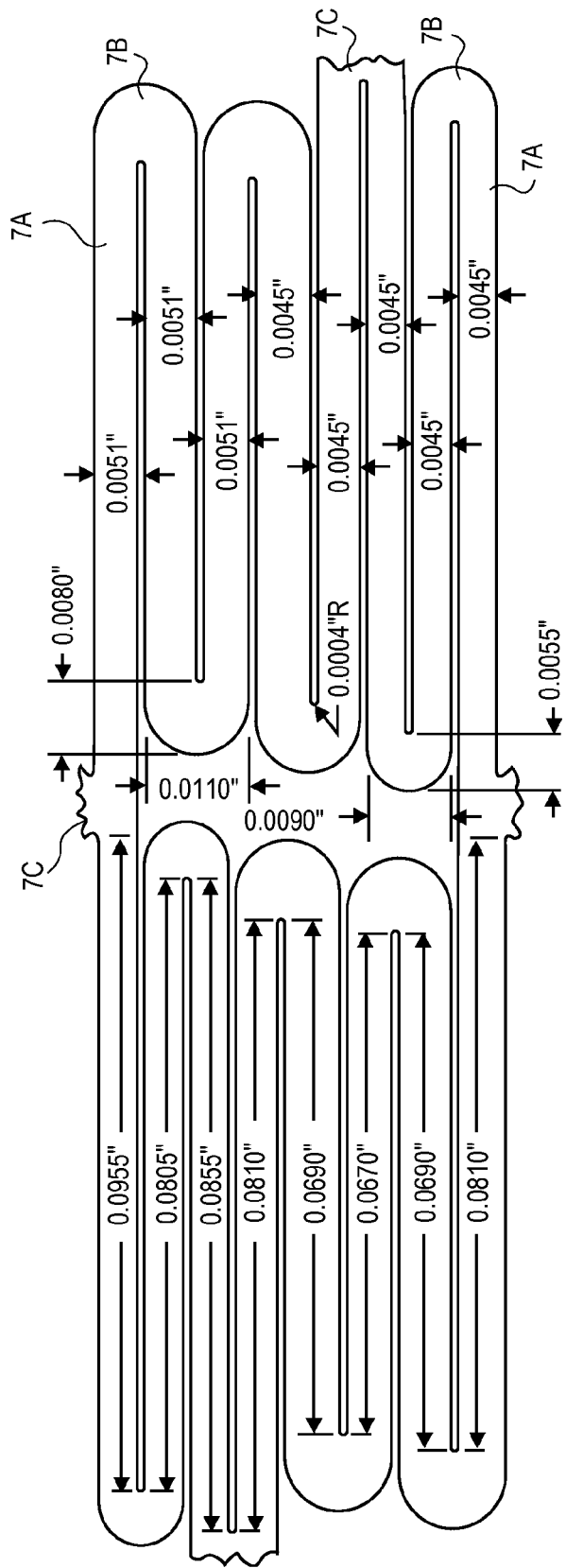

An 8 mm diameter×80 mm long stent having structure as shown in FIG. 7 was laser cut from binary nitinol alloy tubing, diametrically expanded, heat treated, filed, microgrit blasted, electropolished and passivated (hereafter designated as sample 7). The final (nominal) dimensions of each cell of stent sample 7 are shown in FIG. 7; the nominal wall thickness of the stent struts 7A, apices 7B, and connectors 7C was 0.0095 inches. The sample was tested for fatigue life versus competitive stents of the same diameter using the methods described above.

Referring to FIGS. 6 and 7, the stent comprises a series of struts 6A, 7A, apices 6B, 7B, and connectors 6C, 7C forming undulating row patterns in a circumferential direction of the stent. The stent comprises a plurality of such row patterns consecutively in a longitudinal direction of the stent. Except for proximal and distal end rows, each pair of adjacent rows is connected to one another via connectors 6C, 7C to form a cell. For example, as shown in FIGS. 6C, 7C, the cells may comprise eight-lobe cells. Of course, cells with more or less than eight lobes are contemplated by this disclosure. As shown, the connectors 6C, 7C may be positioned at less than all of the apices of each cell. In some aspects, the connectors 6C, 7C may be equally spaced circumferentially about the stent.

In accordance with various aspects of the disclosure, at least one of the struts 6A extending from the connector 6C may have a smaller width dimension than the other strut 6A extending from the connector 6C. For example, one strut extending from the connector 6C may comprise a width of 0.0044 inches, while the other strut extending from the connector 6C may comprise a width of 0.0053 inches. In some aspects, struts 6A extending from the connector 6C may have a longitudinal dimension greater than the next adjacent strut 6A in either circumferential direction from the struts 6A that extend from the connector 6C.

According to various aspects of the disclosure, both struts 7A extending from the connector 7C may have a smaller width dimension than one or more struts 7A spaced from the connector 7C. For example, both struts 7A extending from the connector 7C may comprise a width of 0.0045 inches, while a plurality of struts 7A spaced from the connector 7C may comprise a width of 0.0051 inches. In some aspects, the next adjacent struts 7A in either circumferential direction from the struts 7A that extend from the connector 7C may also have a reduced width of 0.0045 inches. In some aspects, struts 7A extending from the connector 7C may have a longitudinal dimension greater than the next adjacent strut 7A in either circumferential direction from the struts 7A that extend from the connector 7C. In the embodiments illustrated in FIGS. 6 and 7, the cell includes serpentine strut patterns which constitute reverse mirror images as to the right and left side of each cell.

As shown by the data below, samples 6 and 7 demonstrated exceptional fatigue resistance as compared to that of similarly sized competitive stents.

|  | Uni-axial Mean Strain to Failure (%) | Diameter × Length (mm × mm) (for MAPS test) | MAPS Cycles to Failure |
|---|---|---|---|
| Sample 6 | 42.78 | 6 × 80 | 1,719,875 |
| Cordis Smart Stent | 27.22 | 6 × 120 | 320,648 |
| Bard LifeStent | 27.22 | 6 × 120 | 820,191 |
| Sample 7 | 33.89 | Not applicable | Not tested |
| Cordis Smart Stent | 20.56 | Not applicable | Not tested |

Figure 8A:
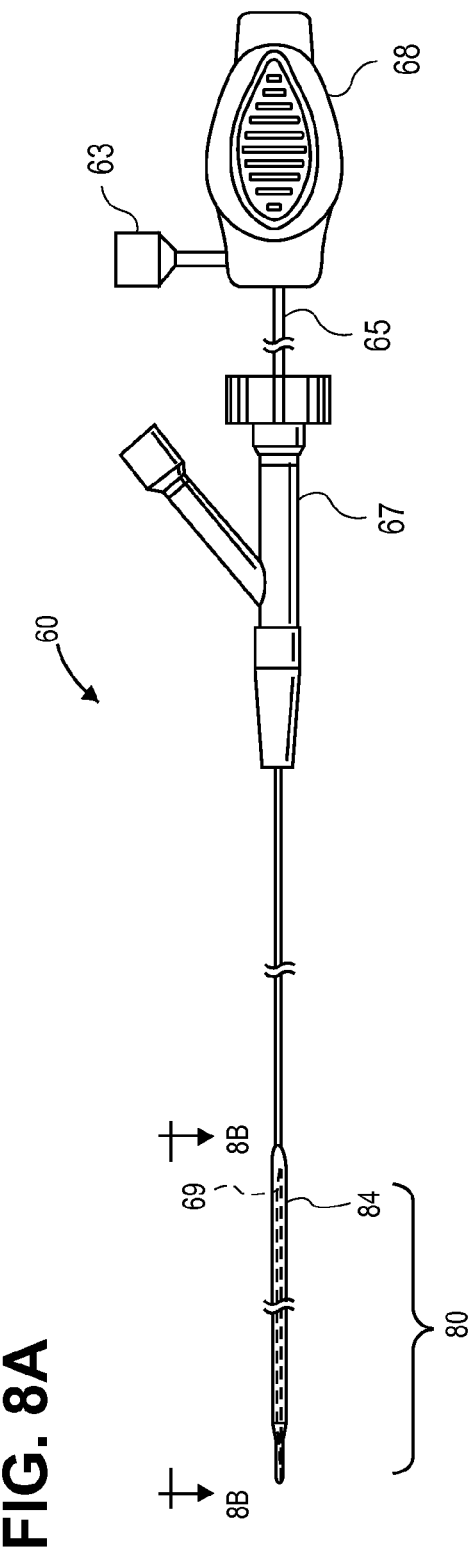
FIGS. 8A, 8B, 8C and 9 illustrate plan views of exemplar delivery systems for fatigue resistant stents.
Figure 8B:
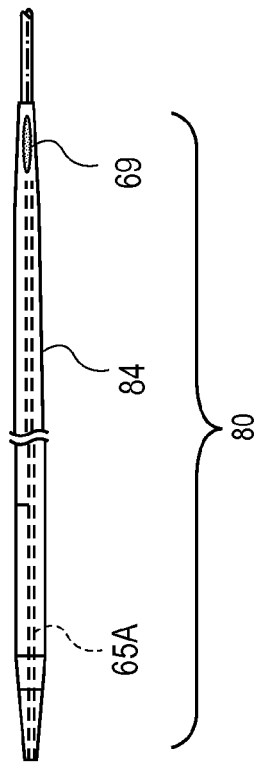
Figure 8C:
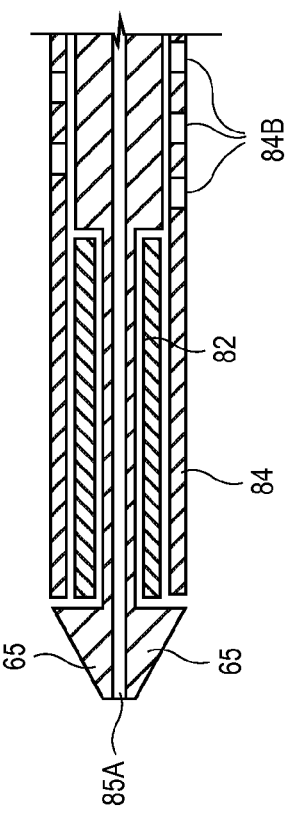

FIGS. 8A, 8B, 8C and 9 illustrate plan views of exemplar delivery systems for fatigue resistant stents. FIGS. 8A, 8B, and 8C illustrate RX delivery system 60 comprised of implant delivery catheter 66 having distal region 80 and stent 82. Implant delivery catheter 66 is comprised of catheter shaft 65, guidewire lumen 65A, proximal guidewire exit skive 69, proximal handle 68, sheath 84 and distal manifold 67. Proximal handle 68 is sealingly attached to catheter shaft 65 and may be comprised of polycarbonate. Catheter shaft 65 is relatively flexible, may be comprised of a polymeric material such as nylon or PEBAX, and may range in length from 60 cm to 300 cm. Catheter outside diameter may range from about 2Fr to about 10Fr. Guidewire lumen 65A diameter may be large enough to allow passage of guidewires ranging in diameter from 0.009" to 0.038". Distal manifold 67 is sealingly attached to sheath 84 and may be comprised of polycarbonate. Sheath 84 may be comprised of braid-reinforced polyester, non-reinforced polymers such as nylon or polyester, or other materials, and adapted to resist kinking and to transmit axial forces along its length. Sheath 84 may be constructed so as to have varying degrees of flexibility along its length. In one embodiment (FIG. 8C) sheath 84 is comprised of weep holes 84B. Weep holes 84B allow annular space between sheath 84 and catheter shaft 65 to be purged of air. Stent 82 may be comprised of stent 40 or other stents.

Figure 9:
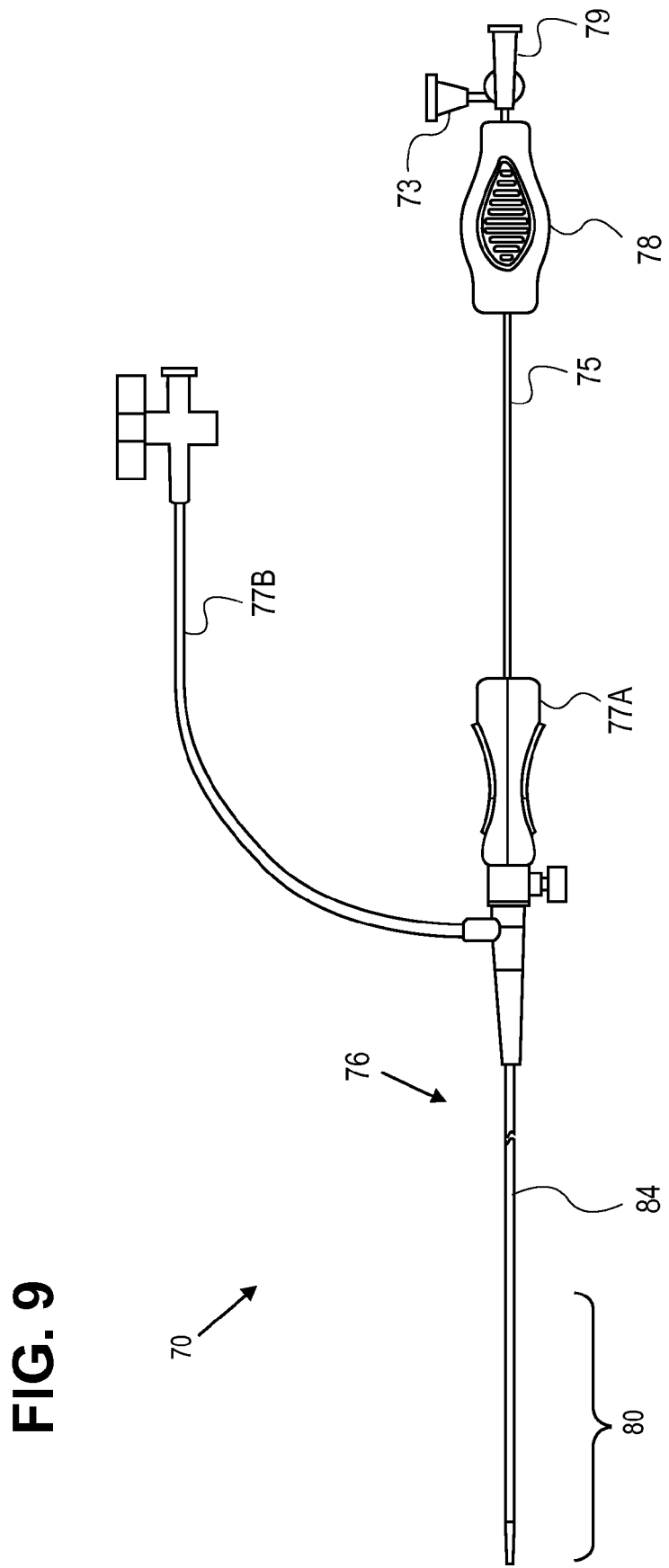

FIG. 9 illustrates OTW delivery system 70 comprised of implant delivery catheter 76 having distal region 80 and stent 82. Implant delivery catheter 76 is comprised of catheter shaft 75, guidewire lumen (not shown), proximal guidewire exit port 79, proximal handle 78, sheath 84 and distal manifold 77A. Sheath 84 may optionally be comprised of weep holes 84B and distal manifold 77A is comprised of infusion tube with stopcock 77B. Catheter shaft 75, guidewire lumen, proximal handle 78 and distal manifold have substantially the same construction, dimensions, and function as catheter shaft 65, guidewire lumen 65A, proximal handle 68 and distal manifold 67 described above in conjunction with FIGS. 7A to 7C. Stent 82 may be comprised of stent 40 or other stents.

Alternate materials for the components of delivery systems 60, 70 are generally well known in the art can be substituted for any of the non-limiting examples listed above provided the functional requirements of the component are met.

An exemplar method of using a stent delivery system to deliver a fatigue resistant stent into a body of a patient is now described. Using techniques well known in the art, a guidewire is percutaneously inserted into a patient's blood vessel and advanced to a region of interest in the patient's body. Using imaging techniques such as fluoroscopy the diseased portion of the vessel is identified and a stent having the correct length and diameter for a treatment site is chosen. With reference to FIGS. 8 and 9 self expanding stent delivery system 60, 70 is advanced over the guidewire to the treatment site and by using imaging techniques such as fluoroscopy the stent, for example stent 40, is positioned at a desired location relative to the treatment site.

Catheter shaft 65, 75 is held stationary and sheath 84 is withdrawn to expose stent 40. Stent 40 expands into contact with a luminal wall of the vessel as sheath 84 is withdrawn. In some methods stent 40 is deployed without being elongated. In other methods the physician elongates the stent during deployment, for example by withdrawing catheter shaft 65, 75 while stent is partially deployed, or by withdrawing sheath 84 quickly, or due to friction of sheath 84 against stent 40 in a tortuous treatment location, or due to other reasons. In one method the stent is elongated 15%. In other methods the stent may be elongated by 10, 20, 25, 30, 35, 40, 45 or 50%. In further methods the stent may be elongated non-uniformly such that some stent cells, for example cells 45', are elongated more or less than the overall elongation of stent 40. In one method the stent cell is elongated 15%. In other methods the stent cell may be elongated by 10, 20, 25, 30, 35, 40, 45 or 50%.

Following implantation of the fatigue resistant stent into a patient, for example stent 40, the patient may return to the implanting physician for a followup visit. During followup the stent may be imaged using imaging techniques such as fluoroscopy, ultrasound, or magnetic resonance imaging to assess whether or not the stent has fractured, or for other reasons.

The invention contemplated is further suitable for stents in addition to those mentioned above. For example, fatigue resistant stents may comprise tapered stents, flared stents, braided stents, bifurcation stents, and other stents as are known in the art. Tapered stents generally have a proximal end of one diameter and a distal end of a second diameter (typically a smaller diameter). Flared stents generally have a short tapered portion at the proximal end of a cylindrical stent, where the flared section is larger in diameter than the cylindrical portion. Braided stents are typically comprised of a tube manufactured by using a braiding method. An example of a braided stent is the Wallstent, sold by Boston Scientific, Natick, Mass. Bifurcation stents are placed in a patient where a vessel branches. Bifurcation stents are generally comprised of a single stent portion that branches into two stent portions and appears similar to a Y-fitting used to connect one piece of tubing to two pieces of tubing.

While the various embodiments of the present invention have related to stents and stent delivery systems, the scope of the present invention is not so limited. For example, it will be appreciated that the various aspects of the present invention are also applicable to other types of expandable implants and their delivery systems. By way of non-limiting example, other types of expanding implants that can benefit from application of the invention include anastomosis devices, blood filters, grafts, stent grafts, support frames for heart valves, vena cava filters, percutaneously implanted valves, aneurism treatment devices, or other devices.

Modifications and equivalents of the disclosed concepts are intended to be included within the scope of the claims. Further, while choices for materials and configurations may have been described above with respect to certain embodiments, one of ordinary skill in the art will understand that the materials and configurations described are applicable across the embodiments.

What is claimed is:

1. A stent for implant in a mammalian body comprising: a tubular structure having an inside diameter, an outside diameter, a sidewall therebetween, a central axis defining a longitudinal direction, and apertures extending through the sidewall, wherein said sidewall is a circumferential sidewall having a wall thickness, said apertures separating struts joined at apices, said apices having a structure to exhibit a level of tensile strain, said struts being generally longitudinally extending and having different widths with a plurality of the struts grouped to define a cell, wherein in the circumferential direction of the stent, each cell comprises a first group of struts having a first width and a second group of struts having a second width different from the first width, with apices that are adjacent in the circumferential direction being offset with respect to one another in the longitudinal direction, said stent having a length along the central axis, wherein elongation of the stent in the longitudinal direction causes a change in the level of tensile strain in the apices, wherein said stent is structured such that when elongated at least 10%, the level of tensile strain in each apex is less than about 3%.

2. The stent of claim 1, wherein when the stent is elongated at least 10%, the level of tensile strain in each apex is less than about 2%.

3. The stent of claim 1, wherein when the stent is elongated at least 20%, the level of tensile strain in each apex is less than about 3%.

4. The stent of claim 1, wherein when the stent is elongated at least 30%, the level of tensile strain in each apex is less than about 3%.

5. The stent of claim 1, wherein when the stent is elongated at least 40%, the level of tensile strain in each apex is less than about 3%.

6. The stent of claim 1, wherein when the stent is elongated at least 50%, the level of tensile strain in each apex is less than about 3%.

7. The stent of claim 1, wherein a tolerance level of tensile strain in each apex is about ±0.5%.

8. The stent of claim 1, wherein at least some of said apices are opposed to one another when the stent is in an unexpanded configuration and are circumferentially offset from one another when the stent is in an expanded configuration.

9. The stent of claim 1, wherein said tubular structure comprises a laser cut tube.

10. The stent of claim 1, wherein said tubular structure comprises a wire joined at regions to form said struts and said apices.

11. The stent of claim 1, wherein said tubular structure comprises a braid.

12. The stent of claim 1, wherein the first group comprises three struts and the second group comprises five struts.

13. The stent of claim 12, wherein adjacent cells are joined together in the circumferential direction by connecting a first strut of the first group to a last strut of the second group, as viewed in the circumferential direction.

14. The stent of claim 12, wherein the struts in the first group have a smaller width and a smaller length than the struts in the second group.

15. The stent of claim 12, wherein the struts in the first group have a greater width and a greater length than the struts in the second group.

16. The stent of claim 1, wherein the apices of the first group have a different width than the apices of the second group.

17. The stent of claim 1, wherein the second width is different from the first width by about 20%.

18. The stent of claim 1, wherein the second width is different from the first width by about 10%.

19. The stent of claim 1, wherein the first group of struts has a length that is different from a length of the second group of struts.

* * * * *